(12) United States Patent
Prais

(10) Patent No.: US 10,267,679 B2
(45) Date of Patent: Apr. 23, 2019

(54) LIGHT SWITCHING INDICATORS BY WAVELENGTH FILTRATION FOR A TESTING DEVICE

(71) Applicant: Ascensia Diabetes Care Holdings AG, Basel (CH)

(72) Inventor: Eugene Randal Prais, West Milford, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

(21) Appl. No.: 15/326,925

(22) PCT Filed: Jul. 20, 2015

(86) PCT No.: PCT/US2015/041105
§ 371 (c)(1),
(2) Date: Jan. 17, 2017

(87) PCT Pub. No.: WO2016/014393
PCT Pub. Date: Jan. 28, 2016

(65) Prior Publication Data
US 2017/0205553 A1    Jul. 20, 2017

Related U.S. Application Data

(60) Provisional application No. 62/028,162, filed on Jul. 23, 2014.

(51) Int. Cl.
*G01J 3/28* (2006.01)
*G01J 3/26* (2006.01)
(Continued)

(52) U.S. Cl.
CPC ............... *G01J 3/28* (2013.01); *A61B 5/157* (2013.01); *A61B 5/150022* (2013.01);
(Continued)

(58) Field of Classification Search
CPC ... G02B 6/0008; G01J 3/26; G01J 3/28; G01J 3/2803; G01J 3/2806; G01J 3/283;
(Continued)

(56) References Cited

U.S. PATENT DOCUMENTS 5,303,037 A    4/1994    Taranowski
5,305,093 A    4/1994    Dosmann
(Continued)

FOREIGN PATENT DOCUMENTS

EP    0299314 A2    1/1989
EP    0866329 A2    9/1998
(Continued)

OTHER PUBLICATIONS

European Patent Office, International Search Report and Written Opinion of International Searching Authority for PCT/US2015/041105, dated Nov. 24, 2015 (9 pages).

*Primary Examiner* — Van T Trieu
(74) *Attorney, Agent, or Firm* — Nixon Peabody LLP

(57) ABSTRACT

A testing system configured to determine an analyte concentration has a user interface that includes a number of visual indicators on its exterior housing. The visual indicators convey different types of information to a user of the testing system when illuminated. Additionally, the indicators are independent of one another in that they can each be illuminated in different colors from one other and turn on and/or off independently of one another. Further, the visual indicators are illuminated using a common lighting element (e.g., a single light emitting diode ("LED")) in combination with one or more waveguides and one or more filters located inside the testing system.

20 Claims, 2 Drawing Sheets

(51) Int. Cl.
    *G01N 21/25*     (2006.01)
    *A61B 5/15*     (2006.01)
    *G01N 33/487*     (2006.01)
    *F21V 8/00*     (2006.01)
    *A61B 5/157*     (2006.01)

(52) U.S. Cl.
    CPC .... *A61B 5/15087* (2013.01); *A61B 5/150824* (2013.01); *G01J 3/26* (2013.01); *G01N 21/25* (2013.01); *G01N 21/255* (2013.01); *G01N 33/48785* (2013.01); *G02B 6/0008* (2013.01); *G02B 6/0028* (2013.01)

(58) Field of Classification Search
    CPC .. G01J 3/284; G01J 3/2846; G01J 2003/1213; G01J 2003/1217; G01J 2003/1221; G01J 2003/1226
    USPC ...... 340/573.1, 691.8, 815.4, 815.45; 604/66
    See application file for complete search history.

(56) References Cited

U.S. PATENT DOCUMENTS

| | | | |
|---|---|---|---|
| 5,349,504 A | 9/1994 | Simms et al. | |
| 5,945,676 A | 8/1999 | Khalil et al. | |
| 6,373,568 B1 | 4/2002 | Miller et al. | |
| 6,630,947 B1 | 10/2003 | Lieberman et al. | |
| 6,741,875 B1 | 5/2004 | Pawluczyk et al. | |
| 6,833,540 B2 | 12/2004 | MacKenzie et al. | |
| 6,879,399 B2 | 4/2005 | Yamauchi | |
| 6,954,260 B2 | 10/2005 | Arnold et al. | |
| 7,154,592 B2 | 12/2006 | Reynolds et al. | |
| 7,483,141 B2 | 1/2009 | Dosmann et al. | |
| 7,701,580 B2 * | 4/2010 | Bassler | G01N 21/05 356/419 |
| 7,820,107 B2 | 10/2010 | Brenneman | |
| 8,373,860 B2 * | 2/2013 | Kiesel | G01N 21/05 356/417 |
| 8,629,981 B2 * | 1/2014 | Martini | G01N 21/05 356/28 |
| 8,940,237 B2 | 1/2015 | Reynolds et al. | |
| 2001/0043780 A1 | 11/2001 | Gancarcik et al. | |
| 2004/0147034 A1 | 7/2004 | Gore et al. | |
| 2008/0218371 A1 | 9/2008 | Joo | |
| 2010/0198142 A1 * | 8/2010 | Sloan | A61B 5/14532 604/66 |

FOREIGN PATENT DOCUMENTS

| | | |
|---|---|---|
| WO | WO 97/41421 A1 | 11/1997 |
| WO | WO 2008/078128 A1 | 7/2008 |
| WO | WO 2013/077624 A1 | 5/2013 |
| WO | WO 2016/014393 A1 | 1/2016 |

* cited by examiner

LIGHT SWITCHING INDICATORS BY WAVELENGTH FILTRATION FOR A TESTING DEVICE

CROSS-REFERENCE TO RELATED APPLICATIONS

This application is a U.S. National Stage of International Application No. PCT/US2015/041105, filed on Jul. 20, 2015, which claims priority to U.S. Provisional Patent Application Ser. No. 62/028,162, filed on Jul. 23, 2014, the contents of each of which is incorporated herein by reference in its entirety.

FIELD OF THE PRESENT DISCLOSURE

The present invention generally relates to analyte testing systems. More specifically, the present invention is directed to user interfaces used in analyte testing systems.

BACKGROUND

The determination of analyte concentrations in body fluids is very important in the diagnoses and maintenance of certain physiological conditions. For example, lactate, cholesterol, and bilirubin levels should be monitored in certain individuals. Additionally, it is important that individuals with diabetes frequently check the glucose concentration in their body fluids to regulate the glucose intake in their diets. The results of such tests can be used to determine what, if any, insulin or other medication needs to be administered.

Testing systems, such as blood-glucose systems, include a meter or instrument used to calculate a glucose concentration value based on a measured output, such as current, and the known reactivity of the reagent-sensing element used to perform the test. Blood-glucose systems typically allow a user to collect a blood sample on a test sensor in which the test sensor is inserted into a test sensor port housing in the meter. The meter measures the reaction between the glucose in the blood sample and a reagent from the test sensor to determine the blood-glucose concentration in the sample.

SUMMARY

A testing system adapted to determine a concentration of an analyte includes a user interface with a plurality of visual indicators. The testing system also includes a lighting element capable of emitting light of a number of different wavelengths corresponding to a number of different colors and a light guide coupled to the lighting element and configured to transmit light emitted by the lighting element. In addition, the testing system includes a first filter configured to filter light of a first wavelength and coupled to a first visual indicator and a second filter configured to filter light of the first wavelength and coupled to a second visual indicator.

Another testing system adapted to determine a concentration of an analyte includes a user interface with a plurality of visual indicators. The testing system also includes a lighting element capable of emitting light of a number of different wavelengths corresponding to a number of different colors and a first light guide coupled to the lighting element and configured to transmit light emitted by the lighting element to one of the plurality of visual indicators. In addition, the testing system also includes a second light guide coupled to the first light guide and configured to transmit light emitted by the lighting element to a second one of the plurality of visual indicators. Further, the testing system includes a first filter coupled to the second light guide, the first filter configured to filter light of a first wavelength being transmitted by the light guide such that the light of the first wavelength is attenuated and to filter light of a second wavelength being transmitted by the light guide such that the light of the second wavelength is transmitted.

A method of illuminating a visual indicator on a testing device includes illuminating a lighting element located inside the testing device and transmitting light along an interior portion of the testing device via a first waveguide. The method also includes filtering a first portion of the light transmitted along the interior portion of the testing device at a first location using a first filter such that the first portion of the light is prevented from being transmitted along a second waveguide coupled to the first location. In addition, the method includes filtering a second portion of the light transmitted along the interior portion of the testing device using a second filter at a second location such that the second portion of light is transmitted along a second waveguide coupled to the second location.

The accompanying drawings, which are incorporated into this specification, illustrate one or more exemplary embodiments of the inventions and, together with the detailed description, serve to explain the principles and applications of these inventions. The drawings and detailed description are illustrative, not limiting, and can be adapted without departing from the spirit and scope of the inventions.

DETAILED DESCRIPTION

As will be discussed in further detail below, a testing system as disclosed herein has a user interface that includes a number of visual indicators on the exterior housing of the testing system. Each of the visual indicators can be illuminated to convey information to a user of the testing system. The visual indicators may be illuminated using a common lighting element (e.g., a single light emitting diode ("LED")) in combination with one or more waveguides and one or more filters located inside the testing system. In some embodiments, the indicators may be independent of one another in that they can each be illuminated in different colors from one other and turn on and/or off independently of one another.

Advantageously, because the visual indicators can be illuminated using a common lighting element, testing systems as disclosed herein can be smaller and less expensive than previous testing systems which required multiple lighting elements to illuminate multiple indicators. Further, because the indicators on the presently disclosed testing systems can be illuminated in different colors from one other and turn on and/or off independently of one another, the presently disclosed testing systems can convey information to users more quickly and clearly than prior displays which were only capable of displaying a single color. Similarly, by illuminating indicators using multiple colors instead of a single color, the presently disclosed testing systems can be more aesthetically pleasing than prior testing systems while avoiding the size and cost disadvantages of prior testing systems which required multiple lighting elements.

Sensor Port Housing

Figure 1:
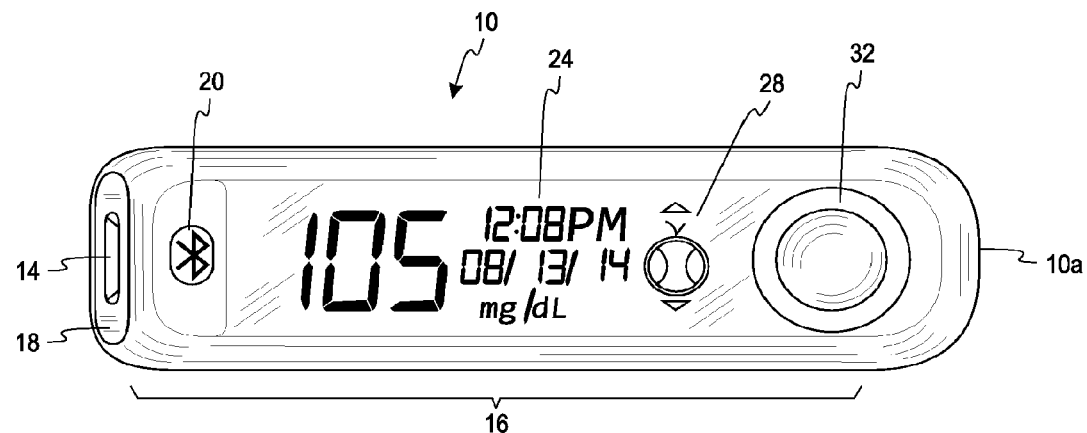
FIG. 1 illustrates a side perspective view of a testing system having an interface for displaying information.

Referring now to FIG. 1, an example testing system 10 includes an exterior housing 10a. The exterior housing 10a includes a sensor port housing 14 that receives a test sensor (not shown) onto which a fluid sample (e.g., a user's blood sample) can be applied for analysis by the testing system 10. For example, in one implementation, a test sensor for receiving a user's blood sample may be inserted into the sensor port housing 14, and the testing system 10 may determine a concentration of an analyte in the blood sample received by the test sensor (e.g., a determination of the glucose concentration of a user's blood sample).

Visual Indicators

The exterior housing 10a of the testing system 10 also includes a user interface 16. As will be described in further detail below, the user interface 16 may include a number of elements that convey information to a user of the testing system 10 and with which the user can optionally interact. For example, as shown in FIG. 1, the user interface 16 of the testing system 10 includes a button which can be used to turn the testing system 10 on or off. The user interface 16 also includes a plurality of visual indicators that provide information about the operation of the testing system 10 to the user.

The visual indicators include a wireless communications indicator 20 that can indicate that wireless communications have been enabled on the testing system 10. Enabling wireless communications on the testing system 10 allows a user to wirelessly transmit and/or receive data from another device as necessary. For example, a user may wish to enable wireless communications on the testing system 10 to wirelessly transmit testing results to another device or computer for viewing or analysis (e.g., analysis by a doctor at a remote location from the user). The wireless communications indicator 20 can then be used to indicate that wireless communications have been enabled. More specifically, in certain implementations, the wireless communications indicator 20 can be illuminated to indicate that wireless communications (e.g., BLUETOOTH® communications, Wi-Fi communications, NFC communications, etc.) are enabled on the testing system 10. Accordingly, the visual indicator 20 remains dark when the wireless communications are disabled or turned off.

The testing system 10 also includes a monitoring indicator 24. The monitoring indicator 24 can be illuminated when the testing system 10 is turned on, during testing, or after testing. In certain implementations, the monitoring indicator 24 can be adjacent to a display that can convey several pieces of information to the user. For example, the display can convey measurement results (e.g., glucose concentration in mg/dL), the current date, and/or the current time. In certain implementations, the display can also communicate hypo- or hyper-glycemic alerts, meal markers, messages about battery life, customer service messaging, etc. A processor (not shown) inside the testing system 10 can control the information displayed on the display. For example, the processor can analyze testing results to display accurate analyte concentrations and/or alerts related to testing results on the display. When the monitoring indicator 24 is illuminated, the information conveyed on the display is visible to a user of the testing system 10. On the other hand, the monitoring indicator 24 can remain dark when there is no information to present via the display.

In addition to the other visual indicators described above, the testing system 10 includes an activity indicator 28 which can be illuminated when a user selects a data marker option via the user interface 16. Data markers allow a user to tag testing device measurements with additional data indicating, for example, conditions under which a measurement was made.

In one implementation, the activity indicator 28 may be illuminated when the user selects an exercise marker option via the user interface. The exercise marker allows a user to indicate that a measurement was taken after a user performed exercise or other vigorous activities. Because exercise and other vigorous activities can significantly affect a user's analyte (e.g., glucose) concentrations, selecting an exercise marker can provide the proper context for someone (e.g., a doctor) reviewing a user's measurement results at a later time.

For example, if a user is participating in vigorous exercise, his glucose concentration levels may drop, and this drop would be reflected in measurements taken by the testing system 10. By selecting an exercise marker to be associated with the measurements, someone (e.g., a doctor) reviewing the measurements at a later time can easily understand when the measurements were taken and how they may have been affected by the user's exercise.

The activity indicator 28 may also be illuminated when a user selects a meal marker option via the user interface 16. The meal marker allows a user to indicate when a measurement was taken in relation to his last meal. For example, one set of meal markers may include a "before food" marker, an "after food" marker, and a "skip" or "none" marker. Because meals can dramatically affect a user's analyte (e.g., glucose) concentrations, selecting an appropriate meal marker can provide the proper context for someone (e.g., a doctor) reviewing a user's measurement results at a later time.

In certain implementations, other types of information (e.g., heart rate, blood pressure, etc.) can be conveyed using the activity indicator 28. A user can select what type of information the activity indicator 28 conveys by interacting user interface 16 to select a relevant information type.

The visual indicators also include a sensor port indicator 18. The sensor port indicator 18 can be used, for example, to illuminate the sensor port housing 14 prior to a user measurement using the sensor port housing 14 (e.g., prior to a user measuring analyte concentration levels using the test sensor 10). Illuminating the sensor port indicator 18 prior to or during a measurement can make the sensor port housing 14 easier to see and therefore, may make it easier for a user of the testing system 10 to properly insert a test sensor into the sensor port housing 14, especially in low light conditions. In certain implementations, the user can illuminate the sensor port indicator by selecting an illumination option via the user interface 16.

The sensor port indicator 18 can also be illuminated after a measurement has been made. More specifically, in certain implementations, the sensor port indicator 18 can be illuminated to quickly convey information about measurement results to the user based on the color of light illuminating the sensor port indicator 18. For example, in an implementation where a user is testing analyte (e.g., glucose) concentration levels, illuminating the sensor port indicator 18 in a blue light ($\lambda < 450$ nm) indicates normal analyte concentrations. Similarly, in certain implementations, illuminating the sensor port indicator 18 in a green light indicates high analyte concentrations, and illuminating the sensor port indicator 18 with a red light indicates low analyte concentrations. In other implementations, other colors can be used to indicate similar concentrations or conditions. Among other benefits, illuminating the sensor port indicator 18 to convey information about measurement results can allow a user more quickly and conveniently analyze results than was possible using prior systems which used monochromatic displays and/or displayed measurement results that were difficult to see.

In certain implementations, the sensor port indicator 18 can be illuminated independently of the other indicators (e.g., the monitoring indicator 24, the wireless communications indicator 20, or the activity indicator 28). For example, in certain implementations, the sensor port indicator 18 can be illuminated while the other indicators remain dark (unilluminated).

Additionally, as will be described in further detail below, in certain implementations, the sensor port indicator 18 can be illuminated in the same color as another indicator (e.g., the monitoring indicator 24, the wireless communications indicator 20, or the activity indicator 28). Having multiple indicators illuminated in the same color makes it easier for a user of the testing system 10 to see notifications and to quickly assess what is being communicated. For example, as described above, in certain implementations, the wireless communications indicator 20 can be illuminated in blue light when wireless communications are turned on. The sensor port indicator 18 can also be illuminated in blue light at the same time as the wireless communications indicator 20. Illuminating both the wireless communications indicator 20 and the sensor port indicator 18 in the same color of light allows a user to easily see that wireless communication are turned on whether the user looks at the sensor port indicator 18 on the side of the device of the communications indicator 20 on the top of the device. Similarly, the sensor port indicator can be illuminated in other colors corresponding to the other visual indicators on the device when the other visual indicators are illuminated.

Further, in certain implementations, all of the visual indicators 18, 20, 24, 28 on the testing system 10 may be illuminated simultaneously to reflect certain alert conditions. More specifically, as described above, a processor (not shown) inside the testing system 10 can analyze testing results to display alerts related to testing results or testing system conditions. Certain alert conditions (e.g, dangerously high or low blood sugar levels, low battery levels, measurement errors, etc.) may require a user's immediate attention. When these alert conditions occur, in certain implementations, some or all of the visual indicators 18, 20, 24, 28 on the testing system 10 can be illuminated simultaneously in a common color (e.g., red) such that a user can easily see that the alert condition has occurred.

Although the testing system 10 includes a sensor port indicator 18, a wireless communications indicator 20, a monitoring indicator 24, and an activity indicator 28, as described above, in other implementations, other visual indicators may be used. For example, in other implementations, additional indicators may be added to a testing system. Further, in certain implementations, the indicators described above may be removed or modified.

Button

In addition to the visual indicators described above, the user interface 16 includes a button 32. The button 32 can be used to power the testing system on or off when the user presses and holds the button 32 down. Similarly, the button 32 can also be used to put the testing system 10 in a sleep mode or wake the testing system 10 from a sleep mode, based on the user's interaction with the button 32. The button 32 of FIG. 1 is circular with raised surfaces, but in other implementations, other shapes can be used.

Lighting Element

Figure 2:
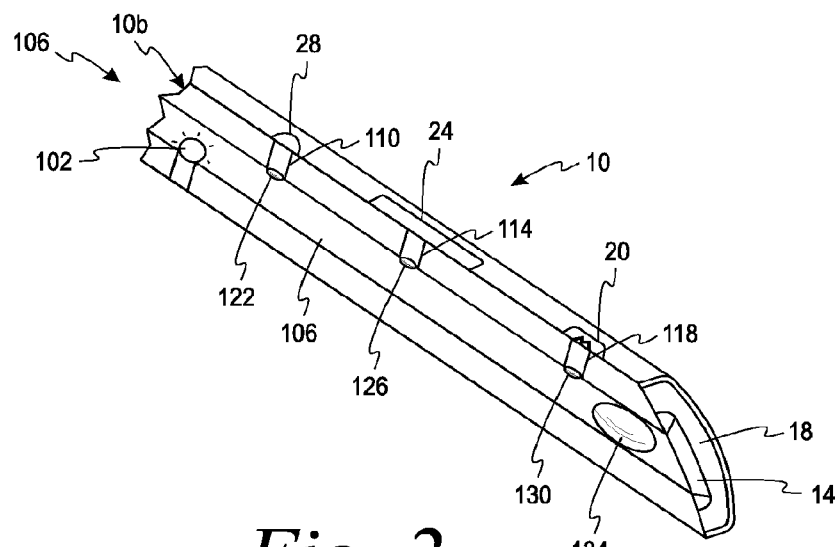
FIG. 2 illustrates a perspective cross-sectional view of a portion of the testing system of FIG. 1.

As shown in FIG. 2, the testing system 10 also includes an interior portion 10b. The interior portion 10b includes a lighting element 102. As mentioned above, unlike other testing systems in which multiple lighting elements are used to illuminate multiple indicators separately within a testing system, the testing systems disclosed herein use a single lighting element 102 to illuminate multiple visual indicators. In certain implementations, the lighting element 102 is a red-green-blue light emitting diode ("RGB LED") or a set of light emitting diodes. In other implementations, the lighting element 102 may be another device configured to emit light of wavelengths corresponding to a plurality of colors. Again, using different colors to illuminate different visual indicators allows a user of the testing system 10 to easily see what alerts or messages are being provided on the user interface 16, based on the displayed color.

Further, as mentioned above, using a single lighting element 102 in the testing system 10 provides a number of advantages over previous testing systems which required multiple lighting elements to illuminate different visual indicators. For example, because only a single lighting element 102 is required to illuminate the multiple indicators 18, 20, 24, 28 located on the exterior housing 10a of the testing system 10, the testing system 10 as disclosed herein can be smaller and may be less expensive than previous testing systems which required multiple lighting elements (which added both size and cost to the previous testing systems) to illuminate multiple indicators.

Light Guides

Coupled to the lighting element 102 is a main light guide 106. The main light guide 106 transmits light along the length of the testing system 10. In addition to transmitting light along the length of the testing system 10, the main light guide 106 also transmits light directly to the sensor port indicator 18 described above with respect to FIG. 1.

In addition to the main light guide 106, the interior 10b of the testing system 10 also includes multiple secondary light guides 110, 114, 118. The secondary light guides transmit light from the main light guide 106 to particular visual indicators on the exterior housing 10a of the testing system 10. More specifically, a wireless communication light guide 118, a monitoring light guide 114, and an activity light guide 110 are each coupled to the main light guide 106 using generally accepted design principles. The activity light guide 110 transmits light from the main light guide 106 to the activity indicator 28. The monitoring light guide 114 transmits light from the main light guide 106 to the monitoring indicator 24. The wireless communication light guide 118 transmits light from the main light guide 106 to the wireless communications indicator 20.

While the main light guide 106 and the secondary light guides 110, 114, 118 of FIG. 2 are rectangular, in other implementations, other shapes may be used for the light guides. Further, each of the light guides 106, 110, 114, 118 can be configured to have a small physical profile such that they easily fit inside the testing system 10. For example, in one implementation, the light guides have dimensions of 3 mm×13 mm×20 mm. Both the main light guide 106 and the secondary light guides 110, 114, 118 can optionally be hollow and transparent and may be made of plastic, copolyester, polycarbonate, or other appropriate materials.

Filters

In addition to the light source 102 and the light guides 106, 110, 114, 118 described above, the interior 10b of the testing system 10 also includes a number of filters 122, 126, 130, 134, respectively. As will be described in further detail below, these filters 122, 126, 130, 134 are coupled to one or more light guides in the testing system 10 and are configured to filter light such that certain colors of light are transmitted to selected visual indicators. In certain implementations, as shown in FIG. 2, the filters 122, 126, 130, 134 are located at the optical coupling points between the main light guide 106 and each of the secondary light guides 110, 114, 118. Optionally, in other implementations, the filters are located between each of the secondary light guides 110, 114, 118 and their respective visual indicators 20, 24, 28.

Through the use of appropriate filters 122, 126, 130, 134, the visual indicators 18, 20, 24, 28 can be illuminated in a desired color or colors. Further, light waves corresponding to unwanted colors are filtered such that they are attenuated or prevented from being transmitted through the filters 122, 126, 130, 134. The testing system 10 incorporates filters 122, 126, 130, 134 configured to filter such that they transmit only light of desired wavelengths at each of the visual indicators 18, 20, 24, 28, and by illuminating certain visual indicators with only certain colors, the testing system 10 allows users to more easily determine what messages are being conveyed via the visual indicators 18, 20, 24, 28 at a glance.

Because the filters 122, 126, 130, 134 in the testing system 10 are designed to only allow light of desired wavelengths to illuminate the visual indicators 18, 20, 24, 28, the visual indicators 18, 20, 24, 28 on the testing system 10 can optionally each display colors distinct from each other, as described above. That is, using appropriately designed filters 122, 126, 130, 134, the monitoring indicator 24, the wireless communications indicator 20, and the activity indicator 28 can optionally be configured to display different colors from each other and/or from the color displayed at the sensor port visual indicator 18.

In certain implementations, the filters 122, 126, 130, 134 incorporated in the testing system 10 can be interference filters or absorptive filters. Further, the filters 122, 126, 130, 134 can be configured to have passbands such that a desired color or colors can be transmitted through each filter's respective visual indicator. For example, in the implementation of FIGS. 1 and 2, the first display visual indicator 20 is configured to be illuminated by blue light when wireless communications are enabled on the testing system 10. Therefore, the filter 130 coupled to this display visual indicator 20 is configured to have a passband corresponding to blue light waves ($\lambda<450$ nm) while blocking other frequencies of light. In certain implementations, the filters 122, 126, 130, 134 may be configured to perform shortpass optical filtration, such that wavelengths longer than a given value will be attenuated or blocked and only the desired color is transmitted. Further, one or all of the filters 122, 126, 130, 134 can optionally be a longpass filter or bandwidth filter. Additionally, the filters 122, 126, 130, 134 may be configured to have sharp cut-on and cut-off transmission slopes.

Optionally, the filters 122, 126, 130, 134 used in the testing system 10 can be configured to have a small physical profile such that they easily fit inside the testing system 10. More specifically, in certain implementations, some or all of the filters 122, 126, 130, 134 are less than 0.05 mm thick. Further, the filters 122, 126, 130, 134 of FIG. 2 have flat physical profiles, but other filter thicknesses and shapes can be incorporated in other implementations.

As for the specific filters in the implementation of FIG. 2, a wireless communication filter 130 is located between the main light guide 106 and the wireless communication light guide 118. As described above, the wireless communication filter 130 is configured to only allow one color of light (e.g., blue light) to illuminate the wireless communication indicator 20. That is, when wireless communications are turned on the testing system 10, the lighting element 102 emits blue light, and the corresponding light waves travel from the lighting element 102 through the main light guide 106 to wireless communication light guide 118. Because wireless communication filter 130 is configured to transmit blue light, the light waves pass through the wireless communication filter 130 and illuminate the wireless communication indicator 20.

A monitoring filter 126 is located between the main light guide 106 and the monitoring light guide 114. Like the wireless communication filter 130, the monitoring filter 126 is also configured to only allow one color of light (e.g., red) to illuminate the monitoring indicator 24, such that when monitoring functions are turned on the testing system 10, the lighting element 102 emits that color of light, and the monitoring filter 126 allows the corresponding light waves to pass, illuminating the monitoring indicator 24.

Additionally, an activity filter 122 is located between the main light guide 106 and the activity light guide 110. Like the wireless communication filter 130 and the monitoring filter 126, the activity filter 122 is also configured to only allow one color of light (e.g., green) to illuminate the activity indicator 28, such that the test sensor 10 is in an activity or exercise mode, the lighting element 102 emits the one color of light, and the activity filter 122 the corresponding light waves to pass through to illuminate the activity indicator 28.

In a preferred implementation, the light reaching the sensor port indicator 18 from the main light guide 106 is unfiltered. That is, no filter is located between the main light guide 106 and the sensor port indicator 18. Because of this, in these implementations the sensor port visual indicator 18 always displays the color of light emitted by the lighting element 102. As shown in FIG. 2, however, in certain implementations, the test sensor 10 includes a sensor port filter 134. Similar to the filters described above, the sensor port indicator 134 is configured to only allow a single color of light to illuminate the sensor port and to block other colors as appropriate.

Further, as mentioned above, the sensor port indicator 18 can optionally be illuminated independently of the other indicators on the testing system 10. For example; in certain implementations, the lighting element 102 can illuminate the sensor port indicator with red light ($\lambda>450$ nm) transmitted via the main light guide 106. As described above, in certain implementations, the sensor port indicator 18 can be unfiltered, while in other implementations, the sensor port indicator 18 can be coupled to a filter configured to transmit red light.

Further, the filters coupled to each of the other visual indicators 20, 24, 28 can be configured to block or attenuate red light from being transmitted. As described above, by allowing the light from the lighting element 102 to illuminate the sensor port indicator 18 in a designated color (e.g., red) while preventing the transmitted light from illuminating the other visual indicators 20, 24, 28, the sensor port indicator 18 can be illuminated independently of the other visual indicators 20, 24, 28 on the testing system 10. In other implementations, the testing device can be configured such that the sensor port indicator 18 is illuminated in other colors (e.g., blue, green, etc.) while the other visual indicators remain dark.

Figure 3:
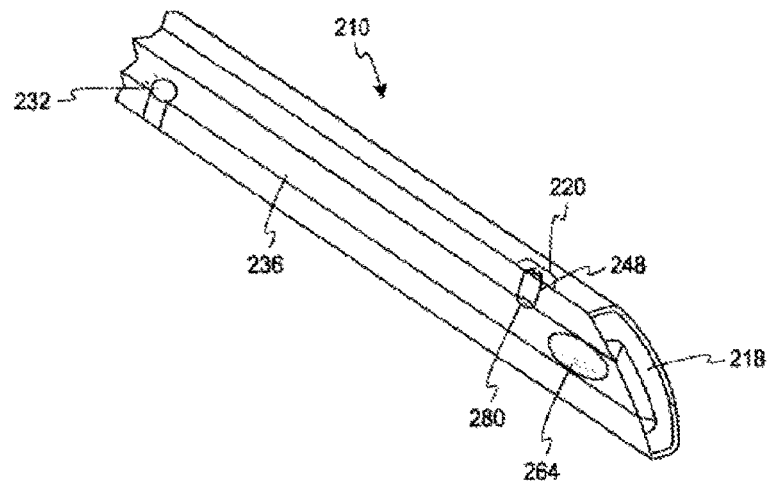
FIG. 3 illustrates a perspective cross-sectional view of a portion of a testing system having an interface for displaying information according to another implementation.

In certain implementations, different configurations of visual indicators, filters, and light guides can be used. For example, FIG. 3 illustrates a perspective cross-sectional view of a portion of a testing system 210 having an interface for displaying information according to another implementation. The testing system 210 includes components similar to those described above with respect to FIGS. 1 and 2, but unlike the testing system 10 described above, the testing system 210 of FIG. 3 includes only two visual indicators 218, 220 instead of four visual indicators 18, 20, 24, 28. More specifically, the testing system 210 includes a sensor port visual indicator 218 and a wireless communications visual indicator 120. A lighting element 132 is located inside the testing system 210. A main light guide 236 is coupled to the lighting element 232 and transmits light to different locations within the testing system 110. The sensor port visual indicator 218 is similar to the sensor port visual indicator 18 described above with respect to FIGS. 1 and 2. Additionally, the light guides 236, 248 and filters 120, 264 of FIG. 3 are similar to the light guides 106, 118 and filters 130, 134 of FIG. 2.

Figure 4:
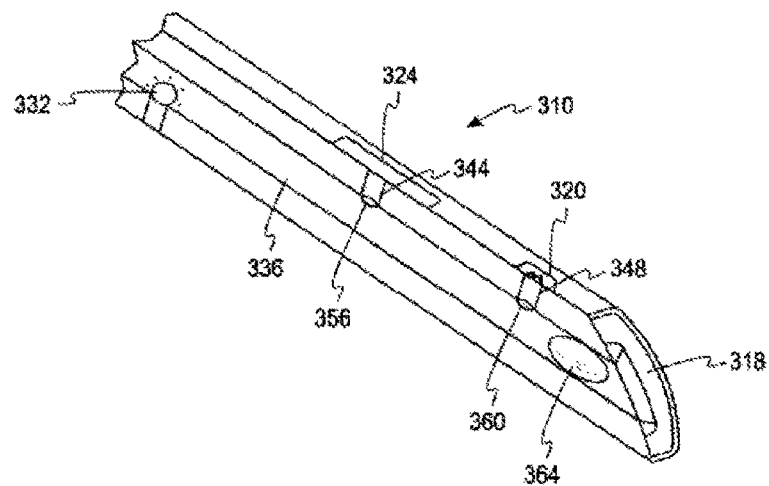
FIG. 4 illustrates a perspective cross-sectional view of a portion of a testing system having an interface for displaying information according to yet another implementation.

FIG. 4 illustrates a perspective cross-sectional view of a portion of a testing system 310 having an interface for displaying information according to yet another implementation. The testing system 310 is also similar to the testing system 10 of FIGS. 1 and 2, but includes only three visual indicators 318, 320, 324 instead of four visual indicators 18, 20, 24, 28. The testing system 310 also includes a lighting element 332, a main light guide 336, secondary light guides 344, 348, and filters 336, 360, 364.

In other implementations, testing devices as disclosed herein may be configured differently than the testing devices described above. For example, certain implementations may have additional or different visual indicators. Similarly, certain implementations may use a different number of filters and/or waveguides to transmit light from a lighting element to one or more visual indicators of interest.

In an exemplary implementation, a user places a blood sample onto a test sensor located in the sensor port housing 14 of the testing system 10 in order to make a glucose concentration measurement. A processor inside the testing system 10 then calculates the user's blood glucose concentration. After calculating the user's blood glucose concentration, the processor programs the monitoring indicator 24 to display the measurement results and programs the lighting element 102 to illuminate in a desired color (e.g., green) such that the monitoring indicator 24 is illuminated.

The lighting element 102 then turns on as instructed by the processor, and the main waveguide 106 transmits light down the length of the testing system 10. As described above, the filters inside the testing system 10 are configured to only transmit certain colors of light while blocking or attenuating other colors of light. In this implementation, because the monitoring indicator 24 needs to be illuminated to display test results, the monitoring filter 126 transmits light while the wireless communication filter 130 and the activity filter 122 prevent the light emitted by the lighting element 102 from illuminating the wireless communication and activity indicators 20, 28, respectively. In a preferred implementation, the sensor port indicator 18 is not directly coupled to a filter, and the sensor port indictor 18 is also illuminated by the lighting element 102. In other implementations, as described above, a sensor port filter 134 may selectively filter certain colors from illuminating the sensor port indicator 18.

Additionally, in other implementations and situations, other indicators can be illuminated as appropriate. For example, after reading his test results in the example above, a user may turn wireless communications (e.g., BLUETOOTH® communications) on such that he can transmit data from the testing system 10 to his personal computer. In this scenario, after the wireless communications have been turned on, the processor programs the lighting element 102 to illuminate in the appropriate color (e.g., blue) such that the wireless communications indicator 20 is illuminated. Further, in certain implementations, multiple indicators are illuminated simultaneously. For example, if the lighting element 102 is an RGB LED, the lighting element 102 may simultaneously emit green and blue light such that the wireless communication indicator 20 and monitoring indicator 24 are illuminated simultaneously while the activity indicator 28 remains dark (unilluminated).

The testing systems disclosed herein offer many advantages over prior testing systems. For example, because the presently disclosed testing systems require only a single light source instead of multiple light sources to illuminate the disclosed visual indicators, the presently disclosed testing systems offer cost savings over prior testing systems. Additionally, using a single lighting source instead of multiple lighting sources frees up space inside the testing system that would have otherwise been taken up by the multiple light sources required by prior systems. Among other benefits, this free space allows other components to fit inside the testing system and allows the testing system to be smaller and lighter than previous systems.

As discussed above, testing systems as disclosed herein have user interfaces that include a number of visual indicators configured to quickly and easily convey information to a user. Unlike prior systems which used monochromatic displays and for which color displays were prohibitively expensive, the presently disclosed visual indicators can operate independently of one another using a common (single) lighting element to convey different types of information to a user. More specifically, the presently disclosed visual indicators can each be illuminated in different colors from one other and turn on and/or off independently of one another using a single lighting element in combination with one or more waveguides, and one or more filters located inside the testing system.

While particular implementations and applications of the present disclosure have been illustrated and described, it is to be understood that this disclosure is not limited to the precise construction and compositions disclosed herein and that various modifications, changes, and variations can be apparent from the foregoing descriptions without departing from the scope of the invention as defined in the appended claims.

What is claimed is:

1. A testing system adapted to determine a concentration of an analyte, the testing system comprising:
    a user interface including a plurality of visual indicators;
    a lighting element operative to emit light of a plurality of wavelengths corresponding to a plurality of colors;
    a primary light guide coupled to the lighting element and configured to transmit light emitted by the lighting element;
    a plurality of secondary light guides configured to transmit light emitted by the lighting element and transmitted by the primary guide; and a plurality of filters, each filter of the plurality of filters being coupled to a separate secondary light guide of the plurality of secondary light guides, each filter of the plurality of filters corresponding to a separate visual indicator of the plurality of visual indicators, and each filter of the plurality of filters being configured to filter light transmitted by the primary light guide,
wherein the plurality of filters includes a first filter coupled to a first one of the plurality of visual indicators and configured to filter light of a first wavelength transmitted by the primary light guide, and a second filter coupled to a second one of the plurality of visual indicators and configured to filter light of the first wavelength transmitted by the primary light guide.

2. The testing system of claim 1, wherein the first filter is configured to transmit light of the first wavelength and the second filter is configured to attenuate light of the first wavelength.

3. The testing system of claim 1, wherein the lighting element comprises a plurality of light-emitting diodes.

4. The testing system of claim 1, wherein each filter of the plurality of filters is coupled between a separate secondary light guide of the plurality of secondary light guides and a separate visual indicator of the plurality of visual indicators.

5. The testing system of claim 1, wherein the second one of the plurality of visual indicators is coupled to a sensor port housing.

6. The testing system of claim 5, further configured to display a first color corresponding to the light of the first wavelength via the first one of the plurality of visual indicators and to display a second color corresponding to a light of a second wavelength via the second one of the plurality of visual indicators simultaneously.

7. The testing system of claim 6, wherein the light of the first wavelength is transmitted to the second one of the plurality of visual indicators via the primary light guide.

8. The testing system of claim 1, further comprising:
a third filter coupled to a third one of the plurality of visual indicators, the third filter configured to transmit light of a second wavelength being transmitted by the primary light guide.

9. The testing system of claim 1, wherein at least one of the plurality of visual indicators displays information relating to an analyte.

10. The testing system of claim 1, wherein each of the plurality of visual indicators displays independent color display behavior.

11. The testing system of claim 1, wherein at least one of the first filter and the second filter has a thickness of less than 0.05 mm.

12. The testing system of claim 1, wherein at least one of the first filter and the second filter is a shortpass filter.

13. The testing system of claim 1, wherein at least one of the first filter and the second filter is a longpass filter.

14. The testing system of claim 1, wherein at least one of the first filter and the second filter is a bandpass filter.

15. A testing system adapted to determine a concentration of an analyte, the testing system comprising:
a user interface including a plurality of visual indicators;
a lighting element operative to emit light of a plurality of wavelengths corresponding to a plurality of colors;
a primary light guide coupled to the lighting element and configured to transmit light emitted by the light element to the plurality of visual indicators;
a first secondary light guide coupled to the primary light guide and configured to transmit light emitted by the lighting element to a first one of the plurality of visual indicators;
a second secondary light guide coupled to the primary light guide and configured to transmit light emitted by the lighting element to a second one of the plurality of visual indicators;
a first filter coupled to the first secondary light guide, between the first one of the plurality of visual indicators and the first secondary light guide, the first filter configured to filter light of a first wavelength being transmitted by the first secondary light guide such that the light of the first wavelength is attenuated and to filter light of a second wavelength being transmitted by the first secondary light guide such that the light of the second wavelength is transmitted; and
a second filter coupled to the second secondary light guide, between the second one of the plurality of visual indicators and the second secondary light guide, the second filter configured to filter light of the first wavelength being transmitted by the second secondary light guide such that the light of the first wavelength is transmitted and to filter light of the second wavelength being transmitted by the second secondary light guide such that the light of the second wavelength is attenuated.

16. The testing system of claim 15, wherein at least one of the plurality of visual indicators is configured to convey information about the concentration of the analyte.

17. The testing system of claim 15, wherein at least one of the plurality of visual indicators is configured to convey information about operation of the testing system.

18. The testing system of claim 17, wherein the at least one of the plurality of visual indicators is configured to convey information about wireless communications on the testing system.

19. The testing system of claim 15, wherein at least one of the plurality of visual indicators is configured to convey an alarm condition.

20. A method of illuminating a visual indicator on a testing device, comprising:
illuminating a lighting element located inside the testing device;
transmitting light along an interior portion of the testing device via a first waveguide;
filtering a first portion of the light transmitted along the interior portion of the testing device at a first location using a first filter such that the first portion of the light is prevented from being transmitted along a second waveguide coupled to the first location; and
filtering a second portion of the light transmitted along the interior portion of the testing device using a second filter at a second location such that the second portion of light is transmitted along a third waveguide, separate from the second waveguide, coupled to the second location.

* * * * *